(12) United States Patent
Bert et al.

(10) Patent No.: US 8,710,445 B2
(45) Date of Patent: Apr. 29, 2014

(54) APPARATUS AND METHOD FOR EVALUATING AN ACTIVITY DISTRIBUTION, AND IRRADIATION SYSTEM

(75) Inventors: Christoph Bert, Aschaffenburg (DE); Eike Rietzel, Darmstadt (DE); Wolfgang Enghardt, Radeberg (DE); Katia Parodi, Heidelberg (DE)

(73) Assignees: GSI Helmholtzzentrum fur Schwerionenforschuntg GmbH, Darmstadt (DE); Siemens AG, Munich (DE); Forschungszentrum Dresden-Rossendorf E.V., Dresden (DE); Heidelberger Ionenstrahl-Therapie (HIT) Betriebs-Gesellschaft AM Universitatsklinikum, Heidelberg (DE)

( * ) Notice: Subject to any disclaimer, the term of this patent is extended or adjusted under 35 U.S.C. 154(b) by 0 days.

(21) Appl. No.: 13/056,184

(22) PCT Filed: Jul. 30, 2009

(86) PCT No.: PCT/EP2009/005512
§ 371 (c)(1), (2), (4) Date: Jun. 10, 2011

(87) PCT Pub. No.: WO2010/015358
PCT Pub. Date: Feb. 11, 2010

(65) Prior Publication Data
US 2011/0309255 A1    Dec. 22, 2011

(30) Foreign Application Priority Data
Aug. 5, 2008 (DE) .......................... 10 2008 036 478

(51) Int. Cl.
*G01T 1/166* (2006.01)

(52) U.S. Cl.
USPC .................................................... 250/363.04

(58) Field of Classification Search
USPC .................................................... 250/363.04
See application file for complete search history.

(56) References Cited

U.S. PATENT DOCUMENTS 7,620,444 B2 * 11/2009 Le et al. .......................... 600/428
2007/0055090 A1    3/2007 Neustadter et al.

(Continued)

FOREIGN PATENT DOCUMENTS

DE    10 2006 024 243 B3    11/2007
WO    WO 2007/079854    7/2007

OTHER PUBLICATIONS

Enghardt et al., Charged hadron tumour therapy monitoring by means of PET, 2004, Nuclear Instruments and Methods in Physics Research A, vol. 525, pp. 284-288.*

(Continued)

Primary Examiner — Christine Sung
(74) Attorney, Agent, or Firm — Reising Ethington PC (57) ABSTRACT

The invention relates to an apparatus for evaluating an activity distribution obtained in a moved target object by a beam that is generated by an irradiation device. Said apparatus comprises: a positron emission tomograph designed to record photons generated in the target object by the beam and generate measurement data representing points of origin of the photons; a movement detection device designed to generate a movement signal representing the movement of the target object; and an evaluation unit designed to associate the points of origin of the measured photons with positions in the target object with the help of the movement signal such that three-dimensional characteristics of the activity distribution actually generated in the target object can be evaluated by means of the photons generated by the beam. The invention further relates to an irradiation system and a method in which such an apparatus is used.

13 Claims, 4 Drawing Sheets

(56) References Cited

U.S. PATENT DOCUMENTS

2010/0108903 A1* 5/2010 Bert et al. .................. 250/396 R
2011/0092814 A1* 4/2011 Yamaya et al. ............... 600/427

OTHER PUBLICATIONS

Nishio et al., Dose-volume delivery guided proton therapy using beam on-line PET system, 2006, Medical Physics, vol. 33, pp. 4190-4197.*

Qiao, Feng, et al. Compensating Respiratory Motion in PET Image Reconstruction Using 4D PET/CT, 2005 IEEE Nuclear Science Symposium Conf Record, XP010896199 ISBN.

Buhler P., et al. An Accurate Method for Correction of Head Movement in PET, IEE Transactions on Medical Imaging, vol. 23 No. 8 Aug. 2004, XP011117922 ISSN, Seiten 1176-1185.

Bert, Christoph, et al. Target Motion Tracking with a Scanned Particle Beam, Medical Physics Letter, 4768 Med. Phys. 34 (12) Dec. 2007, XP012103258 ISSN:0094-2405.

Qiang, Li, et al. Online Compensation for Target Motion with Scanned Particle Beams: Simulation Environment, Physics of Med and Biology, Jul. 24, 2004 XP020023788 ISSN.

Enghardt, W., et al. Charged Hadron Tumor Therapy Monitoring by means of PET, Nuclear Instruments & Methods in Physics Research A 525 (2004) pp. 284-288.

PCT Written Opinion for Serial No. PCT/EP2009/005512 Int. Filing Date: Jul. 30, 2009, GSI Helmholtzzentrum Fur Schwerionenforschung GmbH.

PCT Int. Search Report for Serial No. PCT/EP2009/005512 Int. Filing Date: Jul. 20, 2009, GSI Helmholtzzentrum Fur Schwerionenforschung GmbH.

(German Office Action) Deutsches Patent—Und Markenamt—80297 Munchen dated Apr. 4, 2009 3 pgs.

* cited by examiner

APPARATUS AND METHOD FOR EVALUATING AN ACTIVITY DISTRIBUTION, AND IRRADIATION SYSTEM

The invention concerns an apparatus and a method for evaluating an activity distribution obtained and an irradiation system having such an apparatus. The embodiments of the invention are used particularly in the context of particle therapy and can be used there for monitoring and verification of the activity distribution or the deposited dose distribution.

The particle therapy is an established method for treating tissue, especially tumor diseases. Irradiation processing as used in particle therapy, in particular also the invention-based method subsequently depicted, can even be used in non-therapeutic fields. For example, this includes research work performed with non-living phantoms or bodies, but also in-vitro and in-vivo systems, irradiation of materials, etc. For this purpose, loaded particles, for example, protons or carbon ions or ions of other elements are accelerated to high energies, formed into a particle beam and guided via high energy beam transport system to one or several treatment rooms. In one of said treatment rooms the object to be irradiated is irradiated with the particle beam.

Depending on the energy of the particle beam, the particle beam penetrates the target object and interacts with said target object in a relatively closely defined area, which is preferably located in a previously specified target volume. This has the advantage that compared with other forms of irradiation the area surrounding the target volume can be well preserved. Especially with a scanned particle beam, i.e., a particle beam which is directed successively to different sections of the target object (thus "scanning" the target object) it is possible to achieve a precise dose application.

Irradiating moved target volumes with a scanned particle beam usually requires methods that compensate the movement of the target volume because without taking the movement into consideration it is often not possible to obtain a desired dose distribution in the target object.

Known methods include the method described as Gating, the method described as Tracking, the method described as Rescanning and the fractioned irradiation with a radiation plan which meets additional requirements due to the movement.

In Gating a time frame is determined which is adjusted to the movement of the target volume and during which an application of the beam is obtained, in Tracking the beam is realigned according to the movement of the target volume, and in rescanning a target volume is irradiated repeatedly thus averaging the movement effects.

In addition, a security margin surrounding the target volume is usually applied with irradiations in order to compensate small deviations and changes of position of the target volume compared to an assumed position of the target volume. For example, when irradiating a patient, it is possible to take into consideration changes of position of the patient and changes of position of the region to be irradiated between different irradiation sessions (interfractional changes of position), but also during an irradiation session (intrafractional changes of position).

When irradiating stationary tumors—i.e., tumors that do not move during an irradiation session, for example, subcranial tumors—it is common to use the so-called positron emission tomography. In the context of the present invention positron emission tomography is abbreviated as PET. A PET system detects the photons which are emitted by $\beta^+$ radioactive nuclides. The $\beta^+$ radioactive nuclides, in turn, are generated by the interaction of the particle beam with the material or tissue to be irradiated. Subsequently, it is possible to reconstruct the distribution of the activation caused by the particle beam.

Such therapy monitoring for stationary tumors has been disclosed in the publication Parodi K. et al., "The feasibility of in-beam PET for accurate monitoring of proton therapy: results of a comprehensive experimental study" IEEE Nuclear Science Symposium Conference Record, volume 4, 2004, 2160-2164, or in the publication Parodi K. et al., "Experimental study on the feasibility of in-beam PET for accurate monitoring of proton therapy" IEEE Transactions on Nuclear Science, volume 52, 2005, 778-786, or in the publication Enghardt W. et al., "Charged hadron tumor therapy monitoring by means of PET" Nucl. Instrum. Meth. A525, 2004, 284-288.

In nuclear medicine diagnostics, the use of 4D PET has been disclosed, for example, in the pamphlet Feng Qiao et al., "Compensating respiratory motion in PET image reconstruction using 4D PET/CT" IEEEn Nuclear Science Symposium Conference Record, volume 5, 2005, 2595-2598. For example, here PET data can be reconstructed in such a way that motion information is integrated in the reconstruction process.

The pamphlet Bühler P et al., "An accurate method for correction of head movement in PET", IEEE Trans. Med. Imag. 23, 2004, 1176-1185 discloses a method for movement correction of PET data which takes into consideration a movement of the head during data recording.

It is the objective of the invention to provide an advantageous apparatus and an advantageous method for evaluating an activity distribution generated by a beam in a target object. Furthermore, it is the objective of the invention to specify a respective advantageous irradiation system comprising such an apparatus.

The objective of the invention is achieved by an apparatus in accordance with claims 1 and 8, as well as a method in accordance with claim 10. Advantageous developments of the invention are included in the characteristics of the dependent claims.

The preceding and the following description of the individual characteristics is based on both the procedure category and the apparatus category, even though this is not explicitly mentioned in each individual case. The individual characteristics disclosed in this context can also be important in combinations that differ from those shown in the present invention.

The invention-based apparatus for evaluating an activity distribution occurring in a moved target object, which can be obtained by a beam generated in an irradiation system, comprises the following characteristics:

A positron emission tomograph, which, in particular, comprises detectors that are located opposite each other, and which is designed to record photons generated in the target object by the beam and to generate measurement data representing points of origin of the photons, A movement detection device designed to generate a movement signal representing the movement of the target object, An evaluation unit designed to associate the points of origin of the measured photons with positions in the target object with the help of the movement signal in such a way that three-dimensional characteristics of the activity distribution actually generated in the target object can be evaluated by means of the photons generated by the beam.

Compared with apparatuses of prior art said apparatus makes it possible to monitor $\beta^+$ emitters generated in the target object by the beam, which β⁺ emitters generate in a second step photons, even if the target object to be irradiated moves. Hence the beam induces in the target object an activity distribution, which, in turn, generates photons that can be measured by the positron emission tomograph.

A dose distribution actually deposited in the target object can be tracked via the activity distribution generated and thus via the photons generated in the target object by the beam.

With apparatuses known from prior art it is not possible, or at least insufficient, to monitor in this case a moved target object because the movement of the target object generates fuzziness, making it impossible to evaluate correctly the actually generated activity distribution and thus the actually deposited dos distribution. For example, in a moved tumor the moved anatomy involves also the three-dimensional position and, if necessary, the three-dimensional distribution of the β⁺ emitters. Accordingly, the movement distorts a measurement of the activity distribution induced by the beam. This results in an inaccurate, usually blurred, reconstruction of the activity distribution. If the activity distribution is then used as a basis for determining the actually deposited dose distribution, said fuzziness of the activity distribution would prevent the generation of a three-dimensional characteristic of the deposited dose distribution.

For example, if a deviation is determined between the measured activity distribution and a desired activity distribution, or between the determined dose distribution and a desired dose distribution, it is not possible in a traditional case according to prior art to determine whether this deviation results from an inaccurate deposition of the dose distribution, or whether a movement of the target object during the session of recording the emitted photons is responsible for the deviation.

In the invention-based apparatus the evaluation unit is used to determine the positions in the target object where the photons measured by the PET detectors were generated. For this purpose the movement signal is used. In this way, the movement of the target object can be taken into consideration when evaluating the measurement data. Consequently, in the evaluation process movement-corrected data are determined from the measurement data. This means that the movement of the target object is taken into consideration when reconstructing the activity distribution. This allows for an improved reconstruction, with the goal of achieving a largely perfect reconstruction.

Consequently, this three-dimensional determination of the points of origin of the photons in relation to the target object allows for the possibility of determining the three-dimensional characteristics of the deposited dose distribution (i.e., with the use of the activity distribution generated by the beam) even in a spatially moved target object. If now the activity distribution thus determined deviates from a desired activity distribution it can be concluded that this deviation results from an inaccurate deposit of the dose in the target object. As a result, the measured and movement-corrected activity distribution allows for a better evaluation of the actually deposited dose distribution. In particular it is possible to determine a three-dimensional characteristic of the measured activity distribution.

The movement signal is used to determine the positions in the target object where the measured photons were generated. By means of the movement signal a correlation is determined between the movement of the target object, which is the spatial position of the target object as a function of time, and the PET system, which forms the basis for spatially associating the points of origin of the photons induced by the beam to positions in the target object. For example, the measurement data and the movement signal are recorded in such a way that it is possible to form a temporal correlation between the measurement data and the movement signal. In this case correlation means that the two temporally changeable parameters can be put in relation to one another. It is not intended to restrict the term "correlation" to the second moment of the mutual distribution. For the sake of linguistic simplicity the term "correlation" is used in the application in a more general sense than it is defined in the statistics.

Usually an adequate number of such β⁺ emitters are mainly generated by the particle beam, as, for example, protons, carbon ions or ions of other elements. This includes also ions of radioactive elements, which themselves represent a β⁺ emitter. However, it is also possible that such β⁺ emitters are generated by hard X-ray radiation. See Kluge T. et al., "First in-beam PET measurement of β⁺—radioactivity induced by hard photon beams", Phys. Med. Biol. 52, 2007, N467-N473.

The movement detection device can have different designs and, if necessary, it can be adjusted to the complexity of the movement of the target object and the required accuracy of detection.

In a simple case, the movement detection device can be a sensor by means of which a parameter is measured which is characteristic for the movement, that is, a surrogate parameter. For example, such a sensor can measure the flow of breath (for example, by means of the respiratory temperature), movement of the chest (for example, by means of the circumference of the chest), etc., by means of which a signal is generated from which the movement of the target object can be determined. The PET data measured can now be associated with individual movement phases. For example, this can be done retrospectively. However, it is also possible to detect the movement with the sensor prior to and/or during the generation of photons.

In a more complex design, the movement detection device can also comprise an imaging device, for example, a fluoroscopy system by means of which the movement of the target object to be irradiated, or particularly the target volume within the target object, can be directly monitored. Further embodiments are described in the subsequent description.

However, the movement detection device can simply involve a unit associated with the PET system, which unit generates a signal that characterizes the movement of the target object. Input for said unit can consist, for example, of the sensor signal or the data generated by the imaging device. The movement signal generated by the unit represents movements of the target volume recorded outside of the unit. For example, if the target object has a very regular movement it can be sufficient for the unit to generate a signal that merely represents an anticipated movement of the target object. In this case it would not be necessary to monitor on a continuous basis the movement of the target object by means of an external device, such as a sensor, an imaging device, etc.

In particular, the movement detection device can supply a movement signal that represents the movement of the target object during irradiation. Then the recording of the measurement data with the positron emission tomograph can also be performed during irradiation.

In an advantageous embodiment the positron emission tomograph has a first control unit which has an operative connection with a second control unit of the irradiation device wherein especially the second control unit is able to control the course of irradiation. The first control unit is able to control the data recording of the positron emission tomograph. Because of the fact that the first control unit has an operative connection with a control unit that controls the irradiation device, especially the course of irradiation, for example, the scan process, it is now possible to temporally adjust the data recording with the course of irradiation. In particular, a control of the course of irradiation, for example, the scan process, can simultaneously affect the control of the data recording with the position emission tomograph.

However, this is not absolutely necessary. It is possible to use embodiments wherein the positron emission tomograph records the data only after the irradiation of the target object has been concluded. This is possible because the activation generated by a beam does not immediately subside but can still be detected for a certain period of time. In this case, the data recording with the PET system could be started manually after the conclusion of the irradiation therapy. For this purpose, the PET system can be arranged in the irradiation chamber or in a separate room. It is also possible to generate through irradiation with the particle beam several nuclides with decay times of different lengths. Furthermore, it is possible to determine with the PET system an activity distribution during the irradiation process or after concluding the irradiation therapy.

However, compared with subsequent recording, the recording of measurement data with the PET system during the irradiation process has the advantage that the measured activity distribution is less sensitive to physiological processes (for example, a washout through the blood stream), which, in turn, result in a change of deposited activity distribution. Consequently, the activity distribution changes as a function of time after the conclusion of irradiation.

In an advantageous embodiment, the evaluation unit is also designed to correlate the measured photons temporally with a course of irradiation. For example, with the measurement data of the PET system, it is possible to determine a temporal correlation for the signals of the irradiation process (point in time of irradiation stages as, for example, the transition to a new irradiation point). As a result, it is also possible to ensure a temporal reference to the application of the irradiation plan. In this way, the temporal development of the activity distribution, which is successively generated in the target object through irradiation, can be evaluated and especially compared with the course of irradiation. This allows for an evaluation of the dynamic 4D irradiation process.

Thus the activity distribution generated in the moved target object can be determined and correlated with the course of irradiation, especially with the temporally and/or locally successively deposited single doses. For example, in this way, the three-dimensional characteristics of the deposited dose distribution in the target object can be determined and evaluated at different times during the irradiation process and can be respectively correlated to associated radiation phases.

For example, it is possible in a scan procedure that the incrementally increasing activity distribution (or the successively deposited dose distribution) can be measured in the target object and correlated with the scan process. As a result, it is possible, at least partially, to determine where a particular dose was deposited in the target object, even if the target object is moved. Consequently, it is possible to correlate the PET measurement data with at least part of the grid dots, with at least part of the iso-energy layer or with at least part of the spills (or groups or combinations thereof) for monitoring or reconstructing the dynamic, 4D irradiation procedure. This applies especially when one dose is deposited in an area of the target object which has previously not been irradiated, for example, behind a distal edge of an area already irradiated, at the transition from one iso-energy layer to another iso-energy layer, or when one dose in beam direction is mistakenly deposited behind the already partially irradiated target volume. Thus it is possible to detect and associate, for example, "anomalies".

Usually, this is achieved in that the movement signal, the data recording of the positron emission tomograph and, if necessary, the progress of irradiation is recorded in such a way that the associated data amount are temporally correlatable so that the evaluation unit is able to establish in an easy manner the required temporal correlation. For example, this can be achieved by storing the temporally correlated data in a data collection device in the course of data recording.

In a different model of the embodiment the evaluation unit is designed to determine the movement signal from the recorded measurement data, especially by means of a radioactive marker which is moved by the movement of the target object. In this case the PET system itself functions as a movement detection device.

Alternatively or additionally it is possible that the evaluation unit is designed to determine from the measurement data a further movement signal which also characterizes the movement of the target object and thus is in addition to the movement signal supplied by a movement detection device.

For example, the movement of the target object can be detected by a radioactive marker, which is moved by the target object and the movement of which is recorded by the positron emission tomograph. One or several markers can be firmly connected especially with the target object, for example on its surface and can comprise, if possible, a mostly point-shaped radiation source.

In an advantageous embodiment the evaluation unit is additionally designed in such a way that it can determine from an intensity of the measured photons a quantitative measure for the deposited dose distribution at the positions in the target object. This is now possible because the generated activity distribution in a moved target object can be associated temporally and spatially exactly to positions in the target object.

Therefore, it is possible to use the photons measured by means of the positron emission tomograph to determine the degree of activation at a specific place in the target object, and to reconstruct the deposited dose distribution also in a quantitative manner—at least almost quantitative—and not merely with regard to its three-dimensional elongation.

Moreover, in an advantageous manner the apparatus can also comprise a determining unit which is designed in such a way that the determined activity distribution is compared with a characteristic parameter of irradiation planning.

For example, this can involve the three-dimensional elongation of the activity distribution or the resulting determinable actually deposited dose distribution in relation to the treatment or therapy plan. However, it can also involve a predictive value generated from irradiation planning, which predictive value reflects the anticipated dose distribution or the anticipated activity distribution, which should be possible to be determined or measured by means of the positron emission tomograph. Then the anticipated dose distribution/activity distribution can be compared with the actually measured dose distribution/activity distribution in such a way that deviations can be detected in a simple manner.

To make the comparison easier for the user it is possible to provide a display unit on which the characteristic parameter of irradiation planning and the three-dimensional characteristics of the activity distribution can be displayed together. For example, an image from irradiation planning and the three-dimensional characteristics of the dose distribution can be shown in scale to each another. At the same time, both images can be superimposed or, for example, shown next to each other so that the images can be directly compared with each other. For example, in this way, a verification of security margins can be performed in a simple and effective manner.

An invention-based apparatus as the one described above can be used in an irradiation system which comprises the irradiation device producing the beam.

In addition the evaluation unit can advantageously be designed in such a way that (based on the measurement data which have been detected from the positron emission tomograph) a course of irradiation can be controlled in the irradiation system which is preferably designed as a particle beam system.

In the invention-based method for evaluating an activity distribution generated in the target object and with the help of an apparatus having an optional design according to the invention, a three-dimensional characteristic of the activity distribution is determined by means of a spatial distribution of photons which are measured in a time-resolved manner It is advantageous if, in addition a quantitative measure for the actually deposited dose distribution at the positions in the target object is determined from an intensity of the photons measured. In an advantageous embodiment it is possible to determine also and/or additionally from the distribution of the photons measured in a time-resolved manner even a movement of the target object. The photons measured in a time-resolved manner can even be used to control an irradiation or the course of irradiation.

When the photons are measured in a time-resolved manner, the photons can be associated with different movement phases. In particular, the photons are correlated with said movement phases. The three-dimensional characteristics of the activity distribution generated in the target object can then be separately evaluated for different movement phases.

In the evaluation an anticipated distribution of photons can be determined from a radiation plan. For the static case this has been disclosed in the pamphlet Pönisch F et al., "The modeling of positron emitter production and PET imaging during carbon ion therapy", Phys. Med. Biol. 49, 2004, 5217-5232. However, in systems according to prior art, the application for a moved target object fails because the resulting fuzziness prevents a comparison. According to the invention, the anticipated distribution can be compared with the actually measured spatial distribution of photons, making it easy to detect a deviation between the actual irradiation and a desired status.

In other words, the invention concerns basically also an apparatus for estimating an activity distribution generated by a beam in a moved target object with: a positron emission tomograph for measuring photons generated by the beam in the target object, a movement detection device for generating a movement signal representing the movement in the target object, and an evaluation unit for a mutual evaluation of measurements of the positron emission tomograph and the movement signal for estimating a movement-corrected activity distribution.

In principle, the invention concerns also a method for estimating an activity distribution in a moved target object, comprising the following steps: generating with a beam the activity distribution in the moved target object, measuring with a positron emission tomograph photons generated by the beam in the target object, generating with a movement detection device a movement signal which represents the movement of the target object, and a mutual evaluation of the measurement of the positron emission tomograph and the movement signal for estimating a movement-corrected activity distribution.

Embodiments of the invention and further developments in accordance with the characteristics of the dependent claims are described in more detail by means of the following drawings without, however, being restricted to it. It is shown:

In FIGS. 1 to 4 the same reference numerals will always be assigned to the respective corresponding parts.

Figure 1:
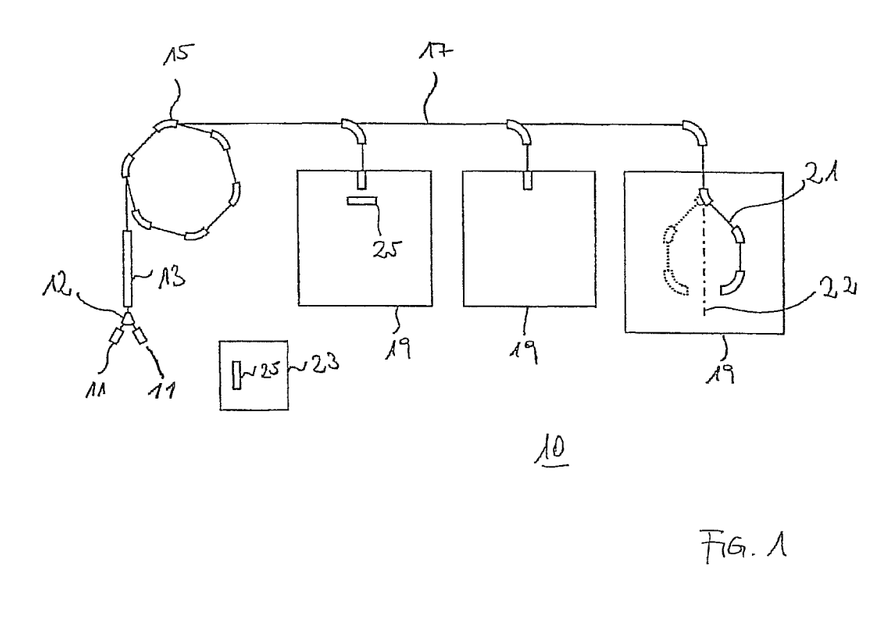
FIG. 1 a schematic structure of a particle beam system,
FIG. 2 a schematic structure of a PET system
FIG. 3 scanning a target volume with a scan procedure,
FIG. 4 a flow chart of an embodiment of the method.

FIG. 1 shows a schematic view of an exemplary structure of a particle beam system 10. In a particle beam system 10 irradiation of a target object, especially irradiation of a human or animal body, especially of tumor tissue, is performed with a particle beam. However, it is also possible to irradiate a material or an object described as a phantom.

The particles used primarily comprise ions, for example, protons, helium ions, carbon ions, ions of other elements or other particles, such as pions. Usually such particles are generated in a particle source 11. For example, said a particle source 11 can be an ion source. If (as shown in FIG. 1) two particle sources 11 are available which generate two different ions of different elements, it is possible to switch between these two types of ions within a short time interval. For example, for this purpose a switching magnet 12 is used which is located between the ion sources 11 and a pre-accelerator 13. For example, in this way the particle beam system 10 can be operated basically simultaneously with protons and with carbon ions, in particular, it can be operated alternatively in short successive time intervals.

The ions generated by the ion source 11 or any ion source 11 and, if necessary, selected by the switching magnet 12, are accelerated in the pre-accelerator 13 to a first energy level. For example, the pre-accelerator 13 is a linear accelerator (abbreviated "LINAC"). Subsequently, the particles are fed into an accelerator 15, for example, a circular accelerator, such as a synchrotron or cyclotron. In the accelerator 15, the ions are accelerated to higher energies as required for irradiation. When the particles have left the accelerator 15, a high energy beam transport system 17 directs the particles to one or several irradiation chambers 19. In the irradiation chamber 19, the accelerated particles are aimed at a target object (not shown) to be irradiated. Depending on the design, this takes place from a fixed direction (in so-called "fixed beam" chambers) or from different directions in relation to the axis 22 via an axially movable and rotatable gantry 21.

In the irradiation chamber 19, the particle beam leaves the beam transport system 17 and impinges a target object to be irradiated which is usually located in the isocenter of an irradiation chamber. The target volume to be irradiated is situated in the target object.

The basic structure of a particle beam system 10 described above is exemplary for particle beam systems but can also have different structures. Consequently, the structure of the particle beam system is not restricted to the scope of the device, the method and the irradiation system. The scope of the invention involves modifications, supplements and/or equivalents.

A PET system 25 is installed in one or several irradiation chambers 19 or even in a different room 23. The subsequent figures explain in more detail the mode of operation of the PET system 25.

Figure 2:
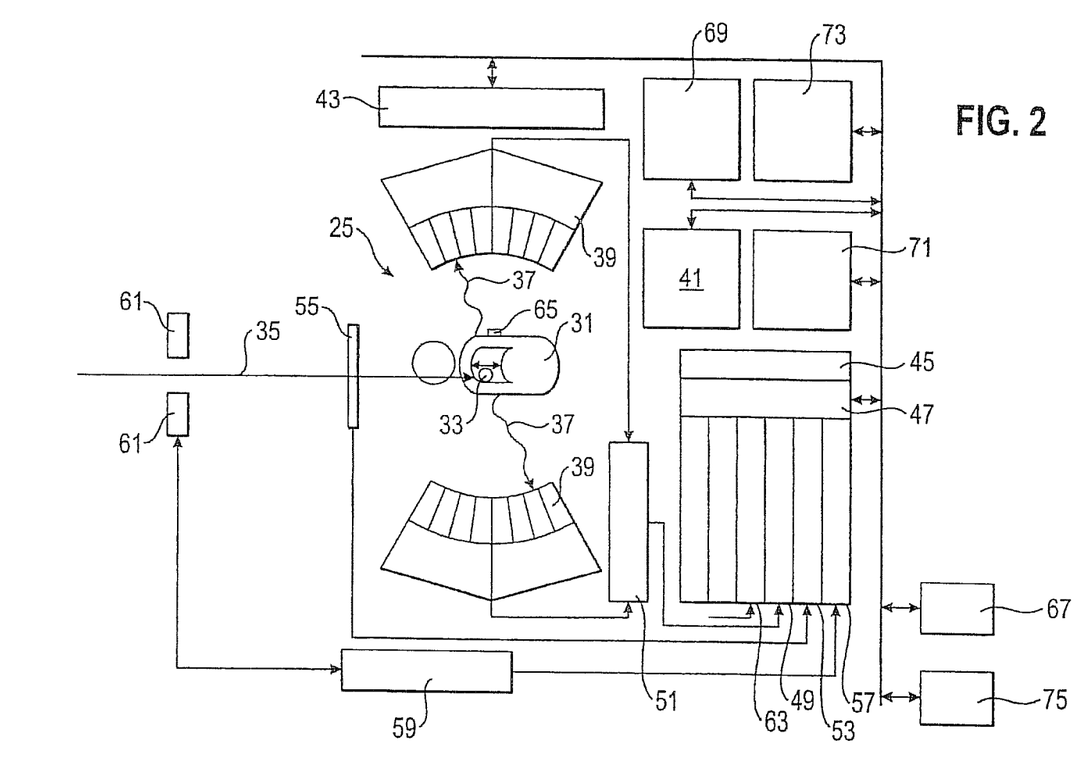

FIG. 2 shows the schematic structure of a PET system 25 which can be used in one of the irradiation chambers 19 and which has an operative connection or interaction with components of the particle beam system 10.

The PET system 25 is used to evaluate an activity distribution generated in a target object 31, for example, in a patient or in a phantom. Said activity distribution allows conclusions to be drawn to the dose distribution actually deposited in the target object 31. The target volume 33, for example, a tumor or a fixed circumscribed area in a phantom, moves during the process of irradiation and while recording the measurement data with the PET system 25.

For example, if the target object 31 is a patient, the movement can be caused by breathing.

By means of a particle beam 35, a previously defined dose distribution is deposited in the target volume 33. The particle beam applied in the target volume 33 interacts with the material of the target volume 33 and generates a distribution of $\beta^+$ emitters which, in turn, emit photons 37 which leave the target volume 33 in opposite direction. The photons leaving the target volume 33 in opposite direction are detected by means of two detector units 39 which are basically arranged on opposite sides around the target volume 33 basically opposing each other.

The PET system 25 is controlled by a control unit 41. Said control unit 41 is connected with other subunits of the PET system 25.

The here depicted division of the individual units and subunits of the PET system 25 and the depicted units of the accelerator system 10 merely show a possibility. It is also possible to arrange the system in different ways. For example, the different functional properties can be integrated in a single control unit or could be distributed in any other manner to subunits that are connected to each other.

These subunits include, for example, a motion control system 43 by means of which the rotation and translation of the PET gantry can be controlled. In this way, the PET system 25 can be positioned in an appropriate manner.

These subunits also include a data recording unit 45 which controls the data recording of the PET system 25. Said data recording unit 45 comprises a data collection unit 47 which, among other things, is used to store the measurement data recorded.

For this purpose, the data recording unit 45 has a first input 49 by means of which measurement data is transmitted to the data recording unit 45, data which has been recorded by the detector units 39 and which has been evaluated with regard to a temporal coincidence of the detected photons with the help of a coincidence processor 51. In this context, the recording of the measurement data is performed especially in a time-resolved manner.

Furthermore, the data recording unit 45 comprises a second input 53 which is connected or coupled with a beam diagnostic system 55. By means of this second input 53, it is possible to enter and store data related to beam properties in the data recording unit 45.

Furthermore, the data recording unit 45 comprises a third input 57 which is connected with a control unit 59 of the particle beam system and which makes it possible that beam parameters used to control the particle beam are stored in the data recording unit 45. For example, the control unit 59 actuates the scan magnets 61 which are used to control the course of irradiation.

Furthermore, the data recording unit 45 comprises a fourth input 63 by means of which a movement signal can be stored. Said movement signal has been recorded by a movement detector 65 and transmitted to a movement detection device 67 of the particle beam system.

By default, the data recording unit 45 is provided with farther subunits such as a central processor (not shown) and memory units (not shown).

In particular, the storage of the different signals and measurement data, which are provided by means of the different inputs of the data recording unit 45, is performed in such a way that they are temporally correlated with each other. Consequently, it can be determined in a subsequent evaluation which state of motion, which phase of the course of irradiation and/or which beam property existed when the measurement data was recorded. This means for example, that every signal and measurement data comprise a time information, and the signal or the measurement data can be correlated to a certain time with said time information.

The movement detection device as a whole is shown here in an exemplary way comprising merely one external movement detector 65. Different movement detection devices can be used: for example, the movement of the abdominal wall can be detected by means of a camera system measuring a movement amplitude of an infrared marker. It is also possible to determine the movement phase from the expansion of a sensor strapped around the belly or the chest. When the method of spirometry is used, the patient breathes through a volume sensor by means of which the volume of the air in- and exhaled by the patient can be determined in a temporally resolved manner. Provision can also be made for a temperature sensor which provides information about the breathing process. The movement detection can also be performed with the help of a small, rice-grain-sized electromagnetic transponder which is implanted in the target volume.

It is also possible to use imaging systems, for example, ultrasound or fluoroscopy, to monitor the movement of the target volume. For this purpose, for example, implanted markers are used which support the recording of the movement in that they can be detected with the imaging system.

Furthermore, provision can be made that the PET system 25 itself detects a radioactive marker used as external movement detector 65 and attached, for example, on the body surface.

The measurement data is evaluated in an evaluation unit 69. At the same time, the evaluation unit 69 is designed in such a way that, contrary to traditional systems used in particle beam systems, the recorded measurement data can be evaluated in particular in a temporally resolved and movement-corrected manner. In this way, it is possible to determine a movement-corrected activity distribution which now allows for drawing conclusions with regard to the actually deposited dose distribution, even in the case of moved target volumes.

Furthermore, the PET system 25 is connected or coupled with a control panel 71 which permits a user to initiate an irradiation and to control and to monitor the course of irradiation.

Furthermore, the PET system is connected or coupled with an irradiation planning system 73 so that the recorded activity distribution can be compared with the parameters included in irradiation planning or with the parameters that can be determined from irradiation planning For example, such a comparison can be performed in a further determining unit 75 designed specifically for this purpose. Said determining unit 75 correlates the data of the irradiation planning system 73 with the data of the PET system 25.

Figure 3:
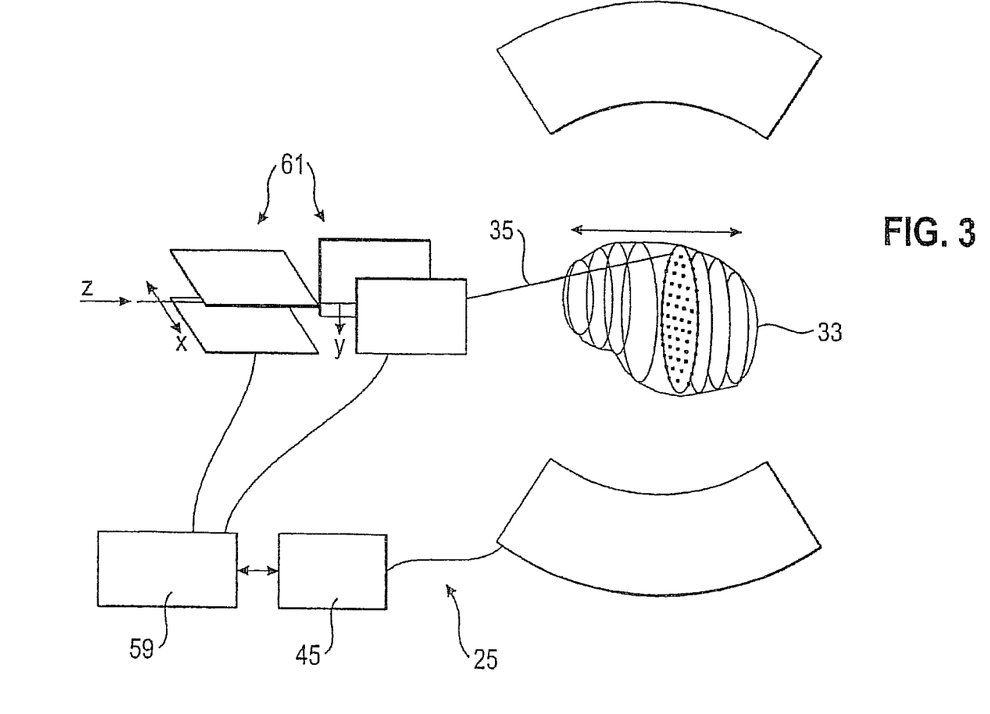

FIG. 3 shows a schematic arrangement of the PET system around a target volume which is irradiated by means of a scan procedure. The irradiation with the scan procedure comprises a particle beam 35 which is dimensioned in such a way that only a single dose can be deposited at a small circumscribed area of the target volume 33. Such a small circumscribed area is a grid dot whereas the parameters of the grid dots are preferably included in irradiation planning. To irradiate the target volume 33 as a whole, different points of the target volume 33, in particular the different grid dots, are irradiated successively, one after another. At the same time, the particle beam 35 is deviated with the help of scan magnets 61 and scanned across the target volume. In the process, the grid dots can be scanned. To irradiate different iso-energy layers, the energy of the particle beam 35 is adjusted appropriately. A target volume 33 is shown wherein three distal iso-energy layers a, b, c have already been irradiated and wherein the particle beam 35 scans the subsequent iso-energy layer d.

Different scan procedures are known, for example, raster scanning wherein the beam scans without stopping between adjacent grid dots across the target volume, spot scanning wherein the procedure is stopped between target points, or continuous scan procedures wherein the beam is deviated continuously.

If necessary, a passive or active energy modulation apparatus can be provided which is not shown for the sake of clarity. For example, said apparatus can be arranged between the scan magnets 61 and target volume 33. By means of the energy modulation apparatus, it is possible to readjust the penetration of the particle beam 35 to a movement of the target volume 33. Alternatively and/or additionally, it is possible to use an energy modulation apparatus that is located before the scan magnets when viewed in beam direction. For example, such an energy modulation apparatus can be used to adjust the energy of the particle beam for different iso-energy layers. The latter procedure is used particularly with particle beam systems having a cyclotron.

Consequently, the scan process results in a temporally protracted irradiation during which the dose to be deposited is incrementally deposited. This dose generates incrementally increasing activity distribution which can be recorded by the PET system 25 in a temporally resolved manner.

Due to the fact that the PET system 25 records the measurement data in a temporally resolved manner and is in an operative connection with the control unit 59 which controls the scan process, the determined activity distribution can be always correlated with the actual scan process. This is possible even when the target volume 33 is moving. As a result, the course of irradiation can be monitored and, if necessary, controlled with the help of the PET system 25 even during complex irradiation processes, as, for example, in the scan procedure with a moved target volume.

Figure 4:
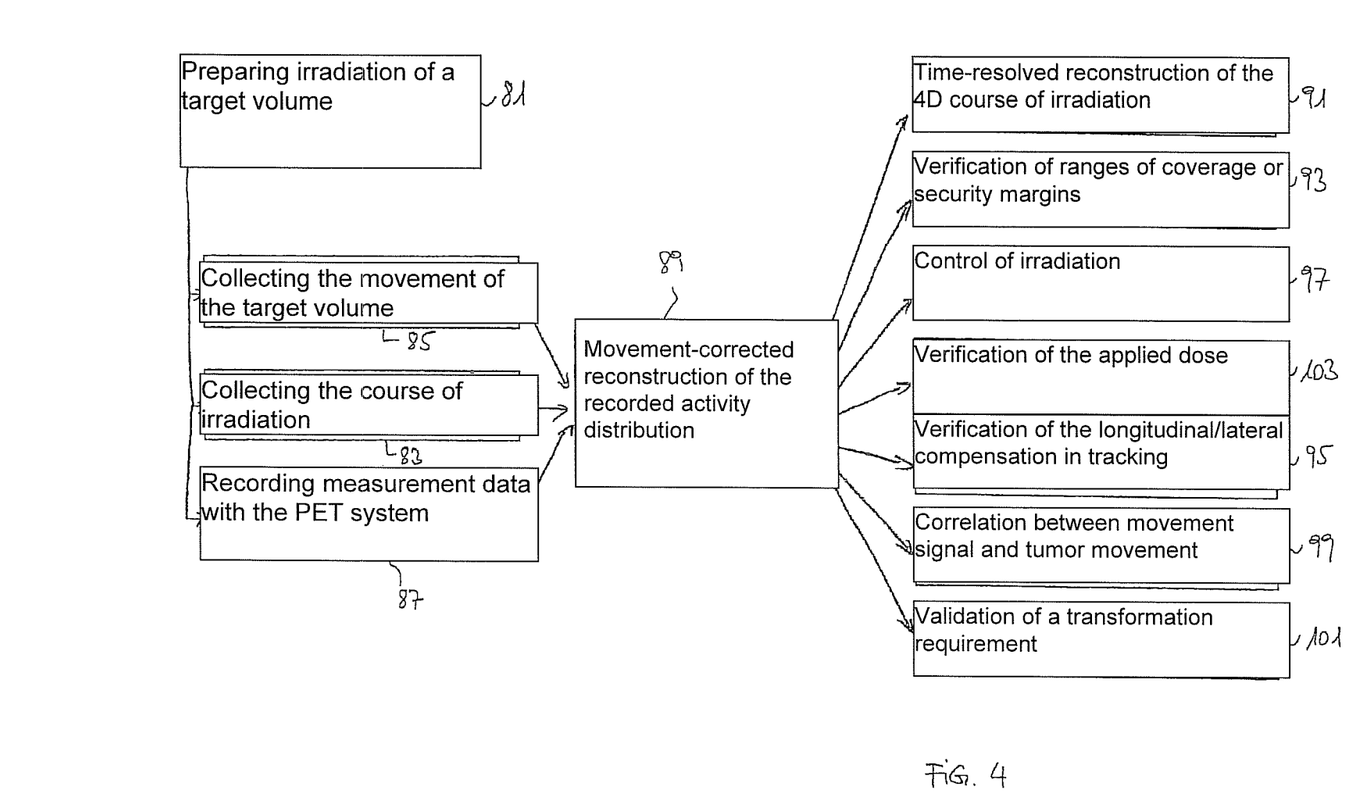

FIG. 4 shows a schematic overview of different process steps which are executed in one embodiment of the process.

At the beginning, irradiation of the target volume is prepared (step 81). Subsequently, the irradiation process is started. In the process, the course of irradiation is recorded (step 83). Furthermore, during the irradiation process, the movement of the target volume 33 is recorded (step 85). In addition, the photons generated through irradiation in the target volume 33 are recorded in a temporally resolved manner with the help of the PET system 25 (step 87).

During irradiation or when irradiation has been concluded, the recorded PET data are evaluated and the activity distribution in the target object 31 on which the data is based is determined. The activity distribution therein is reconstructed in a movement-corrected manner (step 89). This means that during the process of reconstruction the movement of the target object is taken into consideration, reducing or even eliminating fuzziness when determining the three-dimensional characteristics of the activity distribution which results from a movement of the target object 31 during the recording of the measurement data.

Subsequently, several applications are described which can afterwards be performed individually and/or in combination.
Monitoring/Reconstructing the 4D Irradiation Procedure (Step 91)

This has already been described above. In particular, it is possible to correlate the PET signals or the measured activity distribution with at least part of the grid dots, the iso-energy layers a, b, c, d and/or the beam pulses extracted from an accelerator, such as a synchrotron 15 (also described as spill). For example, in this way it is possible to identify inaccurately deposited single doses.
Verification of Security Margins (Step 93)

For example, the method can be used to verify security margins. Security margins are used for irradiation of target volumes 33, in particular of moved target volumes 33, in order to ensure, among other things, that moved target volumes 33 are completely covered with a prescribed dose which has previously been determined and stored in irradiation planning. Since the three-dimensional characteristics of the deposited dose distribution can be determined in a movement-corrected manner with the help of the positron emission tomograph 25, the reconstructed 4D activity distribution shows the coverage of the target region.

A suitable and from a therapeutic point of view very important example is the irradiation of lung tumors. Because of the considerable density difference between the tumor tissue and the healthy lung tissue, it is possible to determine so-called overreaches.

Overreaches occur in places that are located in the security margin, where only part of the tumor comes to lie during the irradiation process. Therefore, overreaches occur mostly at the lateral tumor edges (in relation to the direction of incidence of the particle beam) and are characterized in that the particle beam 35 because of the low density of the tissue in these regions penetrates the target object 31 deeper.

By means of the PET system 25, said overreaches can be detected even in a moved target object without the danger that a movement of the target object 31 interferes with the evaluation of the measurement data. When overreaches disappear completely, it can be assumed that the security margins are at best sufficient or are too small, which is more likely. In this case, the measurement at the tumor should be closely examined in order to determine whether the desired dose distribution has actually been deposited in the tumor.
Verification of Range of Coverage (Step 93)

The method can also be used to verify the range of coverage. Especially when irradiating moved target objects 31, the method of tracking or gating is used. With these methods no, or only minor, distal exceedences of the target volume 33 can be expected which are usually specified in and known from irradiation planning. In rescanning, as well as in passive beam application (beam applications using a collimator and/or an energy modulator adjusted to the target volume) with security margins, ranges of coverage are expected which exceed the distal edge of the target volume 33.

In principle, it is now possible to examine the range of coverage in these moved target objects 31 and target volumes 33. When, in addition, the time of the development of the activity distribution is recorded and correlated with the course of irradiation, it is even possible to state what caused the exceedences, i.e., at which grid dot, at which iso-energy layer, etc. did the exceedence occur.

The analyses when and where which target dose was possibly deposited incorrectly can provide information as to how the irradiation device 10 can be optimized, if necessary.
Verification of the Longitudinal/Lateral Compensation in Tracking (Step 95)

For example, in tracking, especially in longitudinal direction, i.e., in beam direction, the range of coverage of the beam 35 is adjusted during the irradiation process. Depending on the design of the tracking system, this can take place by means of mechanical components, for example, by means of absorber wedges which modulate in a variable manner the energy of the particle beam 35, beam energy for short. This can result in a delayed range modulation, because the mechanical components can perhaps not modulate the beam energy fast enough or not sufficiently accelerated. For example, this can occur when, as a result of a high dose rate, the beam application is very rapidly and/or when the modulation of the energy of the particle beam 35 required from grid dot to grid dot shows large amplitude changes.

Because of the temporal correlation between the developing activity distribution and the course of irradiation, it is now possible to determine which combination of grid dot and movement phase causes problems during tracking. The temporal correlation with all other system parts allows also for the possibility of measuring the temporal delay and using these measurements as respective prediction models. These prediction models, in turn, can be used in irradiation planning. In this way, it is possible to optimize the whole irradiation procedure.

In principle, the same applies to lateral tracking, i.e., a lateral adjustment of the beam position to the movement of the target object 31, wherein lateral tracking can usually be performed easier and faster because lateral tracking does not require the use of any mechanically controlled components.

Control of Irradiation/Adaptive Therapy (Step 97)

The deposited activity distribution measured with the PET system 25 can be used for a direct or indirect control of irradiation (described as image guided radiation therapy).

For example, when the developing dose distribution is measured with the PET system 25 during the irradiation process, it is possible to interrupt the irradiation process as soon as a measurement deviated too much from a target value.

When during fractioned irradiation, i.e., irradiation of the target volume 33 in several self-contained irradiation sessions, the actually deposited dose distribution in this fraction is measured with the PET system 25 after said fraction has been concluded, it is possible based on this knowledge to adjust the irradiation for the following fractions in such a way that an overall dose distribution to be deposited is being applied.

When irradiating a moved target volume 33 by means of rescanning and especially when irradiating with security margins, it is assumed that the interaction between beam and organ movement can result in an inhomogeneous dose distribution, but in a statistic mean the inhomogeneous dose distribution averages over one fraction or more than several fractions. By means of the invention-based apparatus or by means of the invention-based method it is now possible to draw conclusions about the dose distribution actually applied in order to ensure that the desired averaging effect actually takes place.

Because of the temporal correlation between the developing activity distribution and the course of irradiation results it is especially possible to analyze which irradiation phase leads to which effects. At the same time, it is possible to calculate the 4D dose distribution which is determined on the basis of the movement trajectory and the scan progress, i.e., a prediction value for the dose distribution which is measured with the PET system 25. As a result, the actually deposited dose distribution and the anticipated dose distribution can be directly compared section by section of the successive irradiation phases.

It is possible and reasonable to measure not only the accumulative deposited activity distribution by determining, for example, an accumulative deposited 4D activity distribution for a reference situation, but to measure the deposited activity distribution for every movement phase, i.e., as multiple 3D activity distributions.

For example, during irradiation with the gating method, the rising activity degree should only increase during movement phases that lie within the time frame of gating.

Correlation Between the Movement of the Target Volume 33 and Movement Detection Device 65 (Step 99)

In specific irradiation methods, such as gating and tracking, the irradiation is often controlled with the help of a movement signal. The movement signal characterizes the movement of the target volume 33 in that the signal allows conclusions to be drawn with regard to the state of motion of the target volume 33. This conclusion is based on the assumption that the movement signal and the movement of the target volume 33 are correlated to each other. If, for some reason, this correlation no longer exists, this would usually result in the fact that the dose is deposited incorrectly in the target volume 33.

However, occasionally it is the case that the correlation between the movement signal and the movement of the target volume 33 changes. For example, the characteristics of the correlation can change within short periods of time, for example, when a patient with a bronchial carcinoma is coughing. It is also possible that the anatomy gradually changes, for example, when the muscles relax, so that the correlation between the movement and the movement signal experiences a drift.

However, the measurement data recorded in a temporally resolved manner by the PET system 25 allow for a detection of such deviations. When the measurement data is recorded during the irradiation process and is correlated with the course of irradiation, it is especially avoided that the course of irradiation and the recording of the measurement data by the PET system 25 are based on a different correlation.

However, even in the case mentioned last it is possible (if an incorrect correlation between movement signal and movement exists) to arrive at an incorrect evaluation of the deposited dose distribution because of using an inadequate movement signal. Because of the structure of the target volume, for example, because of the special anatomy of the lung involving dense tumor tissue and loose lung tissue, it can nonetheless be assumed that by means of the 4D reconstructed activity distribution it is possible to reconstruct an internal movement trajectory because the particle beam generates more $\beta^+$ emitters in the dense tumor tissue than, for example, in the thin lung tissue. In this way, the target volume 33 can be temporally monitored by means of the measurement data. It is now possible to perform a verification of the correlation between movement signal and movement.

In special embodiments it is possible and reasonable, for example, to attach a radioactive marker on the skin surface the activity of which is visible in the measurement data and which can therefore be used for temporal movement determination. As a result, it is possible to measure also a movement parameter with the PET system.

Validation of a Transformation Requirement (Step 101)

In 4D irradiations and 4D irradiation planning, the radiation plan or irradiation is often based on a transformation requirement which describes the transition between the different movement phases and which allows for an adjustment of the irradiation to the different movement phases. However, in the course of irradiation, especially in the case of a fractioned irradiation, said transformation requirement can change because the anatomical and physiological situation in the patient can change. By means of the invention-based apparatus, it is possible to calibrate the transformation requirement by comparing, for example, in a reference phase, the geometry of the measured activity distribution or dose distribution. Furthermore, it can be estimated whether the anatomy has changed in the reference phase.

Verification of the Applied Dose (Step 103)

Based on the measured activity distribution it is possible to receive information as to how the dose has actually been applied in the target volume 33. It is especially possible to determine from the activity distribution three-dimensional characteristics of the actually applied dose.

The invention claimed is:

1. Apparatus for evaluating a particle beam deposited dose distribution in a moved target object comprising:
   the particle beam for irradiating the moved target object thereby inducing an activity distribution which generates photons in the moved target object,
   a position emission tomograph designed to record the photons generated in the target object by the particle beam and configured to generate measurement data representing points of origin of the photons,
   a movement detection device designed to generate a movement signal representing the movement of the target object, and
   an evaluation unit designed to generate a movement signal representing the movement of the target object, and
   an evaluation unit designed to correlate the points of origin of the measurement photons with positions in the target object using the movement signal in such a way that three dimensional characteristics of the activity distribution actually generated in the target object by the particle beam can be evaluated by means of the photons generated by the beam,
   wherein the evaluation unit is also configured to determine from an intensity of the measured photons a quantitative measure for temporally and/or locally successively deposited single doses at the positions in the target object, and
   wherein the evaluation unit is also configured to determine from the temporally and/or locally successively deposited single doses in a temporally protracted irradiation the particle beam deposited dose distribution in the target object to provide information as to how irradiation can be optimized.

2. Apparatus according to claim 1, wherein the positron emission tomograph has a first control unit for controlling the positron emission tomograph, which has an operative connection with a second control unit of the irradiation device wherein especially the second control unit is able to control the course of irradiation.

3. Apparatus according to claim 1, wherein the evaluation unit is also designed to temporally correlate the measurement data with a course of irradiation, such that changing three-dimensional characteristics of the generated activity distribution in the target object can be correlated with the successive irradiation phases.

4. Apparatus according to claim 1, wherein the movement detection device is designed to generate a movement signal of the target object during an irradiation process.

5. Apparatus according claim 1, wherein the evaluation unit is designed to determine from the recorded measurement data the movement signal or an additional movement signal, which also characterizes the movement of the target object.

6. Apparatus according to claim 1, wherein the apparatus comprises also:
   A determining unit which is designed to compare the determined activity distribution with a characteristic parameter of irradiation planning.

7. Irradiation system with an apparatus according to claim 1 which comprises the irradiation device with which the beam can be generated.

8. Irradiation system according to claim 7 wherein the evaluation unit is also designed to transmit a control signal based on the measurement data with which a course of irradiation in the particle beam system can be controlled.

9. Method for evaluating a particle beam deposited dose distribution in a moved target object, wherein, using an apparatus according to claim 1, a three-dimensional characteristic of an activity distribution generated by a beam in the target object is determined by means of a spatial distribution of the photons induced by the beam, which are measured in a time-resolved manner,
   a quantitative measure for temporally and/or locally successively deposited single doses at the positions in the target object is determined from the intensity of the measured photons, and
   wherein from said temporally and/or locally successively deposited single doses in a temporally protracted irradiation the particle beam deposited dose distribution in the target object is evaluated to provide information as to how irradiation can be optimized.

10. Method according to claim 9, wherein a movement of the target object is determined from the distribution of the photons measured in a time-resolved manner.

11. Method according to claim 9, wherein an irradiation is controlled by using the photons measured in a time-resolved manner.

12. Method according to claim 9, wherein the photons measured in a time-resolved manner are associated with different movement phases, and wherein a three-dimensional characteristic of the dose distribution deposited in the target object is separately evaluated for the different movement phases.

13. Method according to claim 9, wherein an anticipated distribution of photons is determined from a radiation plan, which distribution can be compared with the measured spatial distribution of photons.

* * * * *